United States Patent [19]
Durr et al.

[11] Patent Number: 4,842,478
[45] Date of Patent: Jun. 27, 1989

[54] DENTAL SUCTION APPARATUS

[75] Inventors: Walter S. Durr, Leonberg; Hans-Joachim Hofmann, Remshalden; Andreas B. Bollmann, Ingersheim, all of Fed. Rep. of Germany

[73] Assignee: Dürr Dental GmbH & Co, Fed. Rep. of Germany

[21] Appl. No.: 206,289

[22] Filed: Jun. 14, 1988

Related U.S. Application Data

[63] Continuation of Ser. No. 4,546, Jan. 16, 1987, abandoned.

[30] Foreign Application Priority Data

Jan. 17, 1986 [DE] Fed. Rep. of Germany ....... 3601254

[51] Int. Cl.$^4$ ............................................. F01D 25/32
[52] U.S. Cl. ................................... 415/169.2; 55/204; 55/406; 433/92
[58] Field of Search .............. 415/121 A, 168, 219 C; 55/191, 204, 406, 430; 433/92

[56] References Cited

U.S. PATENT DOCUMENTS

| | | | |
|---|---|---|---|
| 3,091,183 | 5/1963 | Nahrgang | 415/168 |
| 3,138,873 | 6/1964 | Bishop | 433/92 |
| 3,457,645 | 7/1969 | Swanson | 433/92 |
| 4,008,010 | 2/1977 | Fauconnet | 415/219 C |
| 4,102,658 | 7/1978 | Jarvenpaa | 55/406 |

FOREIGN PATENT DOCUMENTS

| | | |
|---|---|---|
| A11766315 | 7/1971 | Fed. Rep. of Germany . |
| 2855653 | 6/1980 | Fed. Rep. of Germany ........ 55/204 |
| 3514331 | 10/1985 | Fed. Rep. of Germany ........ 433/92 |
| A12463748 | 2/1981 | France . |

OTHER PUBLICATIONS

European Patent #23,036, Jan. 1981.
European Pat. #A1 0102000, Aug. 1982.

Primary Examiner—Robert E. Garrett
Assistant Examiner—John T. Kwon
Attorney, Agent, or Firm—Fred Philpitt

[57] ABSTRACT

In an aspirating unit for dental workstations the blower impeller of a vacuum pump (32), a propeller (84) and a pump impeller (68) sit on a common drive shaft (66). The drive shaft (66) is enclosed by a cyclone air extractor (34), the propeller (84) keeping foam components contained in the incoming air and fluid mixture clear of the air discharge connection of the cyclone fluid extractor (34). The pump impeller (68) conveys the fluid discharged at the bottom end of the cyclone fluid extractor (34) forcibly to the fluid outlet connection (28) of the aspirator.

15 Claims, 6 Drawing Sheets

DENTAL SUCTION APPARATUS

This is a continuation of application of Ser. No. 4,546 filed on Jan. 16, 1987, now abandoned.

GENERAL DESCRIPTION

The invention relates to a dental aspirating device.

In known aspirating devices of this type the evacuating pump is connected via a hose to a cyclone fluid extractor spatially separate therefrom. The fluid that is extracted in the cyclone chamber is discharged into the drains via a system of sluices. This means that the discharge end of the cyclone chamber has to lie above the outlet to the drains. However, in many applications it is an advantage to have a completely free choice as to where the cyclone extractor or other air/fluid separating device is installed. Such freedom could, for example, be attained by connecting a fluid pump to the fluid discharge port of the separating device so that the extracted fluid is forcibly conveyed to a higher level. On the one hand, however, this entails a markedly higher equipment outlay for the separating device, and on the other a supply main also has to be run to the separating device to connect up the drive motor of the fluid pump.

The object of the present invention is therefore to provide an improved dental aspirating device whereby forcible discharge of the fluid extracted in the separator is achieved in partial vacuum without the need for an additional drive motor.

In accordance with the invention this object is achieved by an aspirating device as described hereinafter.

In the aspirating device of the invention the air/fluid separating device is combined with the evacuating pump into one unit, and the drive motor provided in any case to move the revolving pump element in the evacuating pump simultaneously turns a pump impeller which forcibly discharges the fluid extracted from the incoming fluid and air mixture, said extracted fluid collecting at the bottom end of the separator.

The aspirating device of the invention can be used as a central aspirator unit for a plurality of workstations. However, it is also very suitable for decentralised direct installation at the workstation, having the advantage of compact construction with few connections required.

Some embodiments of the invention are advantageous from the viewpoint of the aspirator having the smallest radial dimensions possible. Furthermore, the indicated arrangement of the separator necessarily ensures the required height ratio between the separator and the discharge device.

Moreover, in an aspirating device the overhung sections of the shaft are only short and the vacuum pump is axially spaced well away from the separator, so that even if the separator is overfilled for a short time any quantities of fluid that get into its air outlet port do not then find their way directly into the vacuum pump.

Another embodiment of the invention enables stable quantities of foam present in the aspirated air and fluid mixture to be broken up mechanically and so do not get into the air outlet port of the separator.

Other embodiments of the invention are advantageous from the viewpoint of supplying the fluid extracted in the separator to the pump impeller.

In an aspirator according to another embodiment the drive motor which is conventionally only used to operate the vacuum pump can also be used to extract solid particles such as amalgam particles from the quantities of fluid separated from the original mixture, so that the latter do not find their way into the drainage system.

Another embodiment of the invention enables the sludge of solid particles which builds up in the interior of the centrifuge drum to be moved under the action of gravity into the sedimentation chamber beneath the centrifuge drum every time the device is stopped. A clear volume of fluid then collects in the sedimentation chamber over a sediment of solid particles, and when the device is switched back on this clear fluid is pumped back inside the centrifuge through the transfer and return connection carried on the floor of the centrifuge drum.

Another embodiment of the invention means that the discharge pump and, if required, the centrifuge continue operating to remove solid particles even when the inlet port of the whole aspirating device temporarily cannot be subjected to partial vacuum in order not to suck in further quantities of the mixture because the capacity of the separator has been temporarily exceeded, e.g. because there has been an incoming gush of water. In these operating conditions air is temporarily drawn in by the vacuum pump from the surrounding area via the reversing valve.

In another embodiment the reversing valve which is interposed before the inlet of the vacuum pump is controlled using the ouput signal from a fluid level sensor, which is actuated when the fluid in the separator exceeds a preset level.

Another embodiment of the invention enables separation of air and fluid also to be carried out in the centrifuge drum. This separation effect can be obtained over and above that ensured by a cyclone fluid extractor also incorporated, say, in the aspirating device; in many applications.

Another embodiment of the invention is advantageous from the viewpoint of better separation of air and fluid by the separation tube.

In another embodiment of the invention the quantity of fluid removed by the separation tube is passed behind the inner surface of the water ring forming in the centrifuge drum. Thus this quantity of fluid is intensively centrifuged in the centrifuge drum and cannot get to the end flange of the drum directly across the inner surface of the water ring.

The invention is elucidated below with the aid of working examples and with reference to the drawings.

Figure 1:
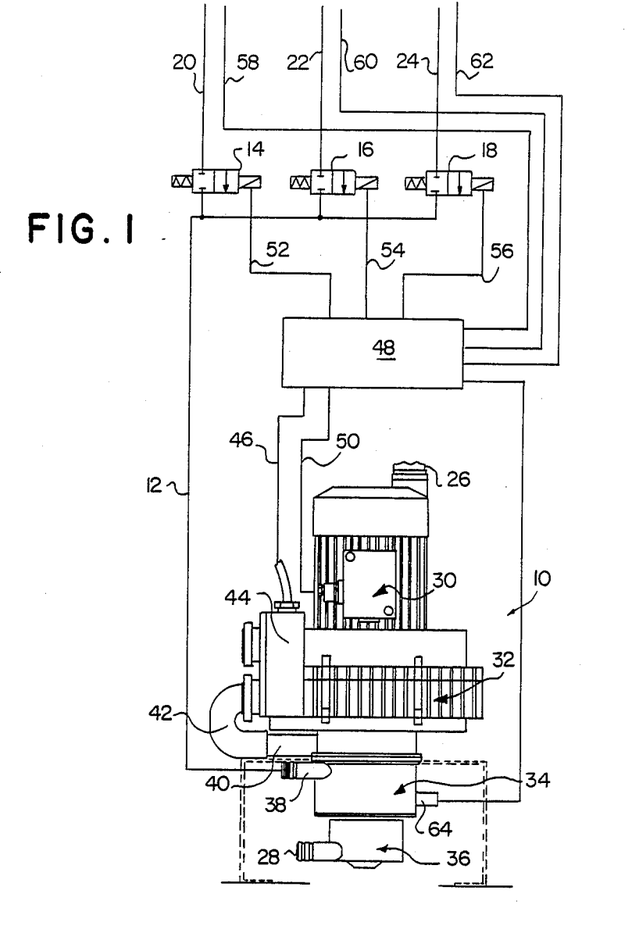
FIG. 1 is a schematic view of a central aspirating system for three dental workstations.

In FIG. 1 an apsirating unit is designated overall by 10 which aspirates and breaks down the mixture of air and fluid (cooling and rinsing water, saliva, blood, etc.) produced at dental workstations. The mixture is fed to the aspirating unit via a collecting line 12, which can be connected via controllable 2/2 valves 14, 16, 18 to lines 20, 22, 24 leading to the individual workstations. The aspirating unit 10 delivers the quantity of air in the aspirated mixture at an air outlet connection 26, which is linked to a line that usually passes over the roof of the building. The quantities of fluid in the mixture are delivered by the aspirator 10 at a fluid outlet connection 26 connected to the drains.

The aspirating unit exhibits an electric driving motor 30, on the base of which is flange-mounted an evacuating pump 32 of in itslef conventional design, which for example exhibits a blower impeller located on a pump shaft. At the botton of the evacuating pump 32 is suspended a cyclone fluid extractor designated overall by 34, which in turn carries a discharge pump 36.

The cyclone fluid extractor 34 has an inlet connection 38 which receives the mixture supplied from the collecting line 12 and a discharge connection 40 which supplies the air once fluid has been removed, said discharge connection 40 being connected via a hose section 42 to one of two inlets of a 3/2 reversing valve 44. The latter's second inlet communicates with the ambient atmosphere, and its working port is connected to the suction port of the vacuum pump 32.

The reversing valve 44 is controlled by a line 46 from a central control unit 48, which also supplies power to the drive motor 30 via a line 50.

Via further lines 52, 54, 56 the control unit 48 controls the operation of valves 14, 16, 18, doing so in response to control signals transmitted via lines 58, 60, 62 from the individual workstations whenever aspiration is required there. Control unit 48 is also linked to the output of a level sensor 64 carried on the periphery wall of the cyclone fluid extractor 34 and actuated when the level of fluid in the cyclone fluid extractor 34 exceeds a present maximum permissible value, meaning that it can no longer be guaranteed that the air discharged from the cyclone extractor is completely free of fluid components. Under these conditions the control unit 48 then switches the reversing valve 44 into the position in which air is aspirated from the ambient atmosphere while the drive motor 30 continues to drive the discharge pump 36. Once the level of fluid inside the cyclone fluid extractor 34 falls back below the maximum permissible level, control unit 48 returns the reversing valve 44 to its normal position, in which the vacuum pump 32 is connected to the discharge connection 40 of the cyclone fluid extractor 34.

Figure 2:
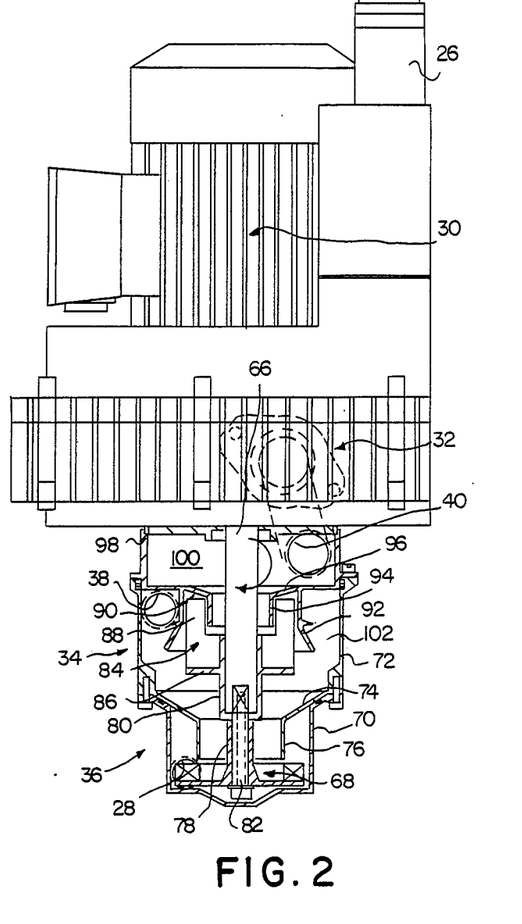
FIG. 2 is an axial partial section through the aspirating unit of the system shown in FIG. 1.

FIG. 2 shows details of the internal design of the aspirator 10. The shaft 66 of the drive motor 30 which at the same time constitutes the pump shaft of the vacuum pump 32 passes through the cyclone fluid extractor 34 and at its free end bears a pump impeller 68 of discharge pump 36. This impeller travels in a cup-shaped pump casing 70, which is tightly screwed to the floor of the casing, designated by 72, of the cyclone fluid extractor 34.

As FIG. 2 shows, the cyclone casing 72 has a conically downward sloping floor 74 bearing a central tubular transfer connection 76. The diameter of the latter corresponds to the blade-free aspirating area of the pump impeller 68 and terminates a short axial distance above the latter. Pump impeller 68, which is made of extruded plastic, has an upwardly extended hub section 78, via which it is braced by means of a screw 82 to the shaft 66, with an interposed propeller hub section 80.

The propeller hub section 80 is part of a propeller, designated overall by 84, which further exhibits a transverse plate section 86 and a plurality of propeller vanes 88 distributed in peripheral direction. The latter travel in a channel 90 which is open at the bottom and is delimited by a bell-shaped deflector section 92 and a tubular connection 94 coaxial to the latter. These last-mentioned stationary parts of the cyclone casing 72 are moulded onto a floor 96 of a cup-shaped casing head element 98, which delimits a discharge compartment 100 communicating with the air exhaust connection 40. the casing head element 98 is screwed tightly to the cyclone casing 72.

As FIG. 2 shows, the inlet connection 38 for the air/fluid mixture terminates immediately below the floor 96 of the casing head element 98 in the periphery wall of cyclone casing 72 and thus communicates with the annular compartment 102 lying between the outer face of the deflector section 92 and the periphery wall of the cyclone casing 72.

The aspirating unit illustrated in FIG. 2 operates in the following manner:

Drive motor 30 turns the blower impeller of evacuating pump 32, propeller 84 and pump impeller 68 jointly, as these parts all sit on shaft 66. As a result of the partial vacuum produced by the vacuum pump 32 the air/fluid mixture is drawn into intake connection 38, and because it has been introduced eccentrically it traverses the interior of the cyclone fluid extractor 34 on a helical path. During this movement the centrifugal force causes the heavy fluid components to be extracted from the mixture and under gravitational force they flow over the conical floor of the cyclone and the tubular connection 76 into the discharge pump 36. The pump impeller 68 thereof forces the extracted fluid components of the mixture into the fluid outlet connection 28. The deflector section 92 prevents parts of the incoming air/fluid mixture from getting straight to the connection 94 and from there into the discharge chamber 100.

Any foam contained in the incoming mixture as a result of foaming constituents is likewise unable to get into the connection 94 because on the way it has to pass through the propeller 84. In the first place the foam is broken up mechanically, and what is more the propeller 84 also sets it in very intense, rapid motion, so that further fluid is extracted as a result of the centrifugal force. This extraction is also particularly effective since the propeller 84 rotates in a direction opposite to the direction of rotation of the mixture's helical course through the cyclone fluid extractor 34. Thus only air from which all fluid components have been removed passes from inside the cyclone casing through the propeller 84 to the connection 94, and from there into the discharge chamber 100.

It will be understood that the aspirating unit 10 has very compact dimensions and that only three flow connections have to be made at the site of use, notably the connection to the collecting line 12, that at the air outlet connection 26 and that at the fluid outlet connection 28. The electrical installation likewise requires only few connections.

It will also be understood that in the foregoing aspirating unit the drive motor 30 is used for three different purposes: to produce the partial vacuum, to forcibly discharge the extracted fluid through the discharge pump 36 and to break up and centrifuge the foam components of the aspirated mixture through the propeller 84.

Figure 3:
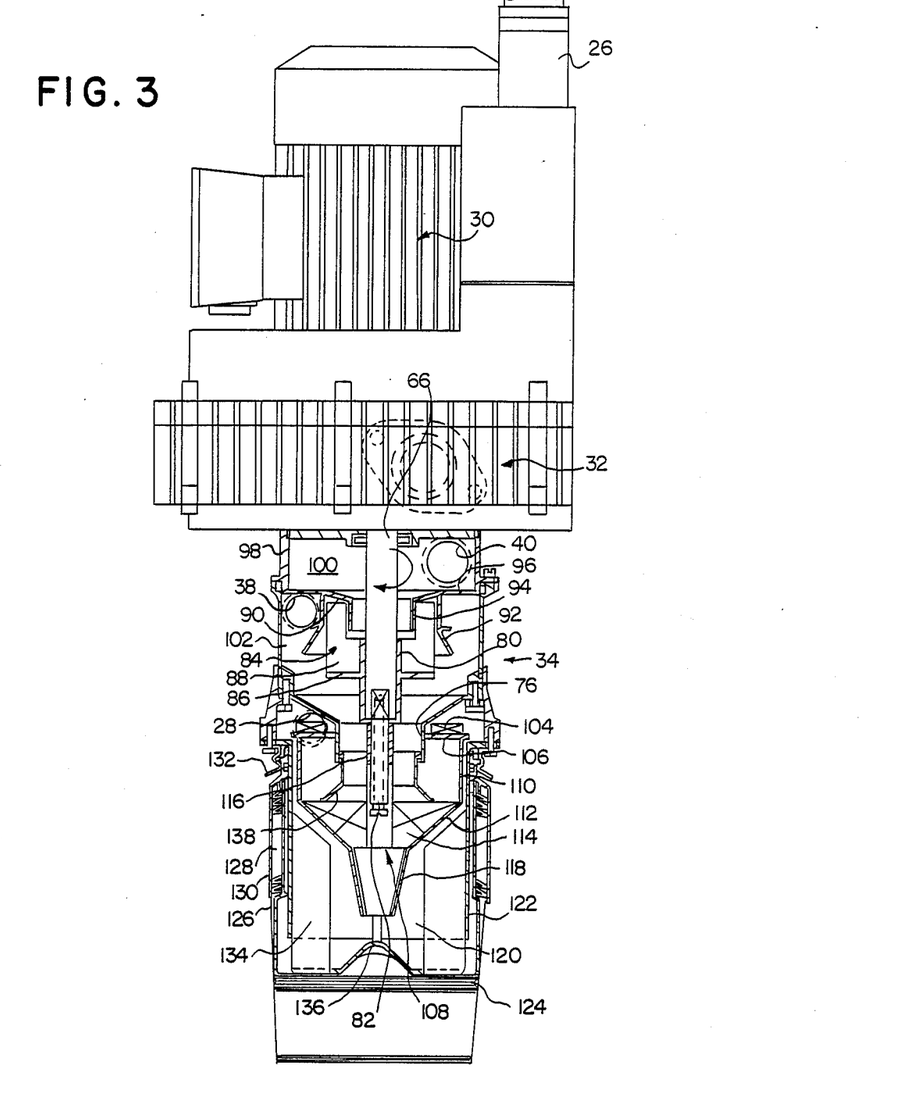
FIG. 3 is a similar sectional view to that of FIG. 2, though showing an aspirating unit with integrated amalgam extraction.

In the modified working example shown in FIG. 3, parts of the aspirating unit 10 that have already been described above with reference to FIGS. 1 and 2 are again identified by the same reference numerals. These parts will not be described in detail again. The main difference between the working example shown in FIGS. 3 and 4 and the working example in FIGS. 1 and 2 is the fact that the pump impeller is designed as part of an overflow centrifuge drum used to remove amalgam particles from the fluid separated from the mixture.

In the aspirator shown in FIG. 3 pump vanes 104 positioned on the end face of an annular top end flange 106 of a centrifuge drum designated overall by 108 form a pump impeller to forcibly expel the extracted fluid.

Centrifuge drum 108 has a cylindrical periphery wall 110, at the top end of which is fixed radially inward projecting end flange 106, and a conically downward sloping floor 112, which is connected via several vanes 114 radially distributed in circumferential direction to a hub section 116. The latter is again braced with the shaft 66 by means of a screw 82, with the propeller 84 interposed.

A central section of the floor 112 of the centrifuge drum 108 bears a conical, downward tapering transfer and return connection 118, which projects into a settling chamber 120 located below the centrifuge drum 108 and tightly delimited in part by a cylindrical sedimentation casing 122, open at the bottom, and in part by a collecting sachet 126 tightly sealed at the bottom by a transverse weld seam 124. The collecting sachet is tautly drawn over the outer surface of the sedimentation casing 122, with a reverse 128 of tubular sachet material arranged in a zig-zag coil in the interior of a cartridge 130, pushed tautly onto the outer face of the sedimentation casing 122 and axially fixed by stirrup springs 132. The sedimentation casing 122 is joined tightly to the pump casing 70, which is now designed to be open at the bottom.

A plurality of smoothing vanes 134 are provided inside the sedimentation chamber 120, the vanes lying in radial planes in peripheral distribution, moulded onto the inner wall of the sedimentation casing 122 and terminating at a distance before the centrifuge drum 108. At their base the smoothing vanes 134 are connected by a conical distribution section 136, which is likewise an integrally extruded part of the sedimentation casing 122 and whose purpose is to distribute in peripheral direction amalgam sludge falling under the action of gravity when the drive motor 30 is stopped from the periphery wall 110 of the centrifuge drum 108 via the floor 112 of the latter and the transfer and return connection 118 into the sedimentation chamber 120.

Figure 4:
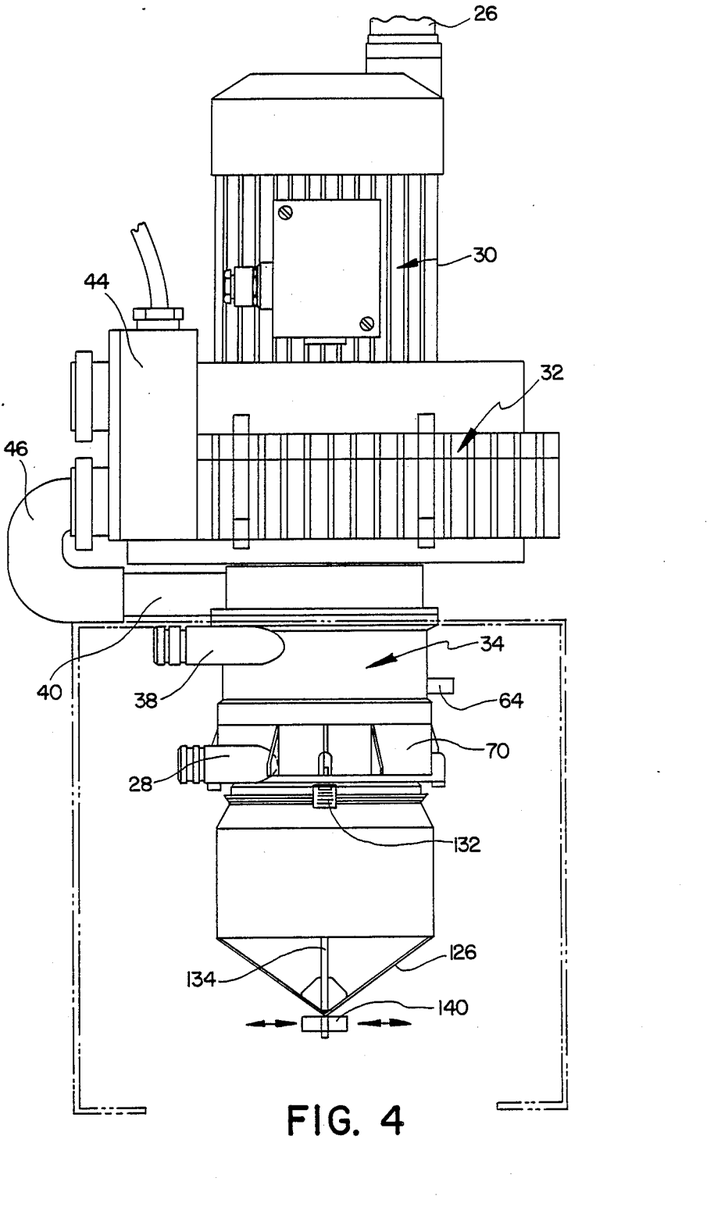
FIG. 4 is a side view of the aspirating unit of FIG. 3, turned by 90 degrees.

The basic mode of operation of the aspirating unit shown in FIGS. 3 and 4 is similar to that of the aspirating unit described above with reference to FIGS. 1 and 2. However, the extracted fluid components of the mixture supplied via the collecting line 12 are conducted into the interior of the centrifuge drum 108 by connection 94, which is extended as far as directly above the top edge of the vanes 114 by a further connection element 138 extending conically at its lower end. Inside the centrifuge drum the fluid is set in rapid motion by the vanes 114, and under the action of the centrifugal force the amalgam particles carried along in the fluid are deposited on the periphery wall 110. Purified water flows across the annular compartment, which is delimited by the inner edge of end flange 106 and the outer face of connection 94, into the pump casing 70 and is forced into the fluid outlet connection 28 by the pump vanes 104.

If the drive motor 30 is switched off at the end of the working period the amalgam sludge retained in the centrifuge drum 108 then falls into the sedimentation chamber 120, as described above. There the amalgam particles contained in the sludge are deposited under the action of gravity, and a relatively clear layer of fluid forms over the resulting sediment. This layer of fluid is then pumped back from the transfer and return connection 118 into the interior of the centrifuge drum 108 when drive motor 30 is started up again.

Once a given amount of amalgam has been deposited in the collecting sachet 126, the latter is pulled off axially downwards and sealed at its top end by a further transverse weld seam, for which purpose, as shown in FIG. 4, the aspirating unit exhibits two welding rods 140 which can be moved perpendicular to the apparatus axis.

Figure 5:
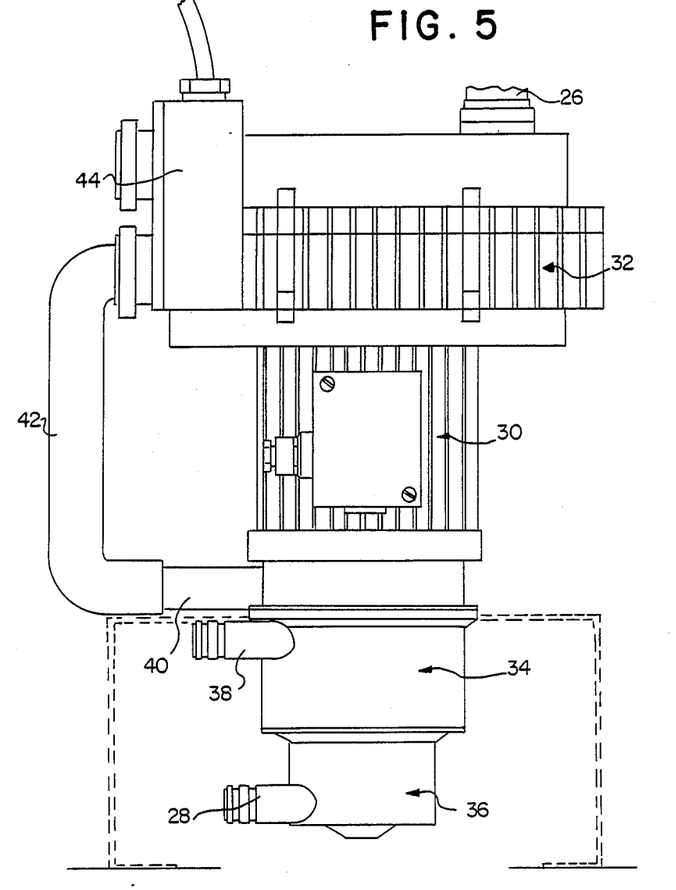
FIG. 5 is a side view of an aspirating unit which has been further modified.

FIG. 5 shows a further modified working example derived from the aspirating unit in FIGS. 1 and 2 in that the cyclone fluid extractor 34 and the discharge pump 36 supported by it are positioned on one end of drive motor 30. The internal design of cyclone fluid extractor 34 and discharge pump 36 is exactly the same as shown in FIG. 2.

In the working example shown in FIG. 5, however, the motor shaft is also drawn out over the second end face of the motor casing and carries the blower impeller of the vacuum pump 32, which is now positioned on the second end face of drive motor 30 at the top in FIG. 5.

In this manner a greater axial, vertical distance is obtained between the vacuum pump 32 and the cyclone fluid extractor 34, so that even when the cyclone fluid extractor 34 is charged with great quantities of gushing water no fluid gets into vacuum pump 32; hose section 42, which is now longer, is available as an additional buffer section.

For the remainder the aspirating unit according to FIG. 5 operates in the same way as that shown in FIGS. 1 and 2.

Figure 6:
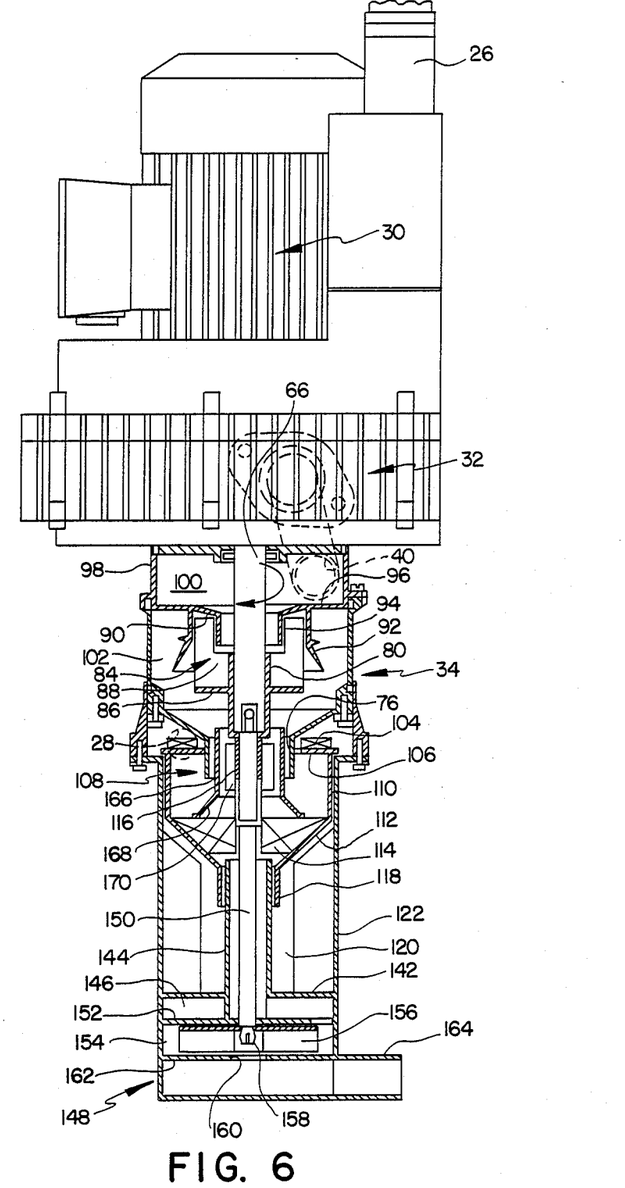
FIG. 6 is a similar section to that in FIG. 3 through an aspirating unit which has been further modified.

In the aspirator of FIG. 6 parts that have already been described above with reference to FIG. 3 are again identified by the same reference numerals. The parts concerned will not be described again in detail. The main difference between the aspirating unit of FIG. 6 and that of FIG. 3 is the fact that the mixture of air, fluid and solid particles produced at the workstation is supplied from below. The sedimentation casing 122 is designed as a fixed part and has a floor 142 which delimits the settler 120. From this floor a central guide tube 144 extends upwards, penetrating the transfer and return connection 118 and running to just above the floor 112 of the centrifuge drum 108. The interior of the guide tube 144 communicates with an outlet compartment 146 of a feed pump designated overall by 148, which is positioned on the base of the sedimentation casing 122. To simplify matters the pump casing and sedimentation casing 122 are represented in the drawing as an integral part; it will be evident that in practice these comprise several cup-shaped extrusions assembled together. Screw 82 now has an elongated head in the form of shaft 150. Shaft 150 extends through the guide tube 144 and traverses a top end wall 152 of a pump chamber 154 in sliding play. In the pump chamber rotates a pump wheel 156, which is detachably snapped onto a slotted end section 158 of the shaft 150. Pump wheel 156 aspirates the mixture produced at the workstation via a central opening 160 in a lower end wall 162 of the pump chamber 154, said mixture being passed via a hose (not shown) to an inlet connection 164 of the aspirating unit.

A separation tube 166 is connected, locked against rotation, to the centrifuge drum 108. The separation tube is similar in shape to the connector element 138 and has a bottom separation tube section 168 expanding conically downwards. The free rim of the latter is at a greater distance from the drum axis than the inner rim of stop flange 106. The separation tube 166 is connected via radial arms 170 to the hub section 116 of the centrifuge drum 108.

In the aspirating unit shown in FIG. 6 the incoming mixture of air, fluid and solid particles is conveyed from feed pump 148 through guide tube 144 into the lower end of centrifuge drum 108. Here the vanes 114 set the mixture in rapid motion, the light air components and foam components migrating towards the drum axis, while the heavy fluid components and solid particles migrate towards the periphery wall 110 of the centrifuge drum 108. The air thus extracted enters the inside of the separation tube 166 along with foam constituents, the arms 170 carrying the separation tube 166 producing a further intense centrifugation. Fluid thus formed passes through the conically expanding separation tube section 168 back into the interior of the centrifuge drum 108.

The air and any remaining foam components are discharged from the top end of separation tube 166 into the interior of cyclone extractor 34, where a further extraction of fluid takes place. The latter is due on the one hand to the swirling air motion, and on the other to the action of the propeller 84. Thus only air from which fluid components have been eliminated enters the outlet connection 40.

We claim:

1. A dental aspirating unit comprising
    (1) a vacuum pump (32) exhibiting a rotating pump shaft (66),
    (2) a drive motor (30) operating on said pump shaft (66),
    (3) an air/liquid cyclone extractor (34) which is provided at spaced points of its casing with
        an inlet port (38) for the air/liquid mixture, and
        an outlet port (40) for air from which liquid has been expelled, and
        a liquid discharge port (76) formed in its base section,
    (4) a motor driven discharge pump (36) receiving liquid from the liquid discharge port (76) of said cyclone extractor (34) and including a discharge pump causing (70) and a pump impeller (68) rotating therein; characterized in that
        (a) the air/liquid cyclone extractor (34), the vacuum pump (32) and the discharge pump (36) are coaxially combined into one unit and the vacuum pump (32) and the discharge pump (36) are both driven by the only drive motor (30);
        (b) the liquid discharge port (76) defined in the funnel shaped base section of the cyclone extractor (34) lies above and is aligned with the suction hub portion of the pump impeller (68) which rotates about a vertical axis coinciding with the axis of said liquid discharge port (76) so that liquid removed from the mixture in the cyclone extractor (34) flows under gravitational force into the discharge pump (36) and the surface of the mass of liquid contained in the discharge pump casing under gravitational force is established in a horizontal plane being parallel to the plane of motion of the pump impeller (68).

2. An aspirating unit as set forth in claim 1 wherein the liquid discharge port (76) of the cyclone extractor (34) is arranged in a central section of the floor (74) of the cyclone casing and the cyclone extractor (34) is positioned tightly on the pump casing (70) coaxial to the pump impeller (68; 104, 106) and in turn carries the vacuum pump (32).

3. An aspirating unit as set forth in claim 1 wherein the cyclone extractor (34) is coaxially positioned on one end of the drive motor (30) and in turn likewise coaxially carries the discharge pump (36) while the vacuum pump (32) is positioned coaxially on the other end of the drive motor (30).

4. An aspirating unit as set forth in claim 1 wherein the drive shaft (66) carrying the pump impeller (68) extends into a top section of a casing (72) of the cyclone extractor (34) and there carries a propeller (84) equipped with vanes (88) which freely pass between an air discharge connection (94) and a deflector element (92) coaxially enclosing the latter at a distance.

5. An aspirating unit as set forth in claim 1 wherein a floor (74) of the casing (72) of the cyclone extractor (34) slopes downwards to the center of the floor.

6. An aspirating unit as set forth in claim 1 wherein a floor (74) of the casing (72) of the cyclone extractor (34) carries a central connection (76) terminating just above the aspirating section of the pump impeller (68).

7. An aspirating unit as set forth in claim 1 wherein the pump impeller (68) is formed by a top end flange (106) and pump vane (104) of a centrifuge drum (108) positioned thereon, said centrifuge drum being positioned on the drive shaft (66).

8. An aspirating unit as set forth in claim 7 wherein beneath the centrifuge drum (108) is disposed a sedimentation chamber (120) with which the interior of the centrifuge drum (108) communicates via a transfer and return connection (118) carried by the drum floor (112).

9. An aspirating unit according to claim 7 wherein the cyclone extractor (34) includes a separation tube (166) rotating with the centrifuge drum (108) and coaxial to the drum axis which passes through the end flange (106) of the centrifuge drum (108) with radial clearance.

10. An aspirating unit according to claim 9 which includes a bottom separation tube section (168) that expands in conical form.

11. An aspirating unit according to claim 10 wherein the rim of the bottom separation tube section (168) is spaced further from the drum axis than the inner rim of the end flange (106).

12. An aspirating unit according to claim 1 which includes a controllable reversing valve (44) via which the aspiration port of the vacuum pump (32) can be optionally connected to the ambient atmosphere instead of to the air discharge port (40) of the cyclone extractor (34).

13. An aspirating unit according to claim 1 which includes a liquid level sensor (64) incorporated in the cyclone extractor (34) by means of whose output signal the reversing valve (44) is controlled.

14. An aspirating unit according to claim 1 wherein the inlet port (38) of the cyclone extractor (34) is linked to a collecting line (12) to which a plurality of workstation lines (20 to 24) are connected.

15. An aspirating unit according to claim 14 wherein the workstation lines (20 to 24) are connected via a controllable separation valve (14 to 18) to the collecting line (12).

* * * * *